United States Patent
Loftus et al.

(10) Patent No.: US 7,135,172 B1
(45) Date of Patent: Nov. 14, 2006

(54) BUCKY PAPER AS A SUPPORT MEMBRANE IN RETINAL CELL TRANSPLANTATION

(75) Inventors: David J. Loftus, Palo Alto, CA (US); Theodore Leng, Mountain View, CA (US); Philip Huie, Cupertino, CA (US); Harvey Fishman, Menlo Park, CA (US)

(73) Assignee: The United States of America as represented by the Administrator of the National Aeronautics and Space Administration, Washington, DC (US)

( * ) Notice: Subject to any disclaimer, the term of this patent is extended or adjusted under 35 U.S.C. 154(b) by 647 days.

(21) Appl. No.: 10/238,515

(22) Filed: Sep. 4, 2002

(51) Int. Cl.
*A01N 63/00* (2006.01)
*A61F 2/14* (2006.01)
*A61F 2/00* (2006.01)

(52) U.S. Cl. .................... 424/93.7; 424/427; 623/4.1

(58) Field of Classification Search ............... 424/93.7, 424/427
See application file for complete search history.

(56) References Cited

OTHER PUBLICATIONS

S. Yamamoto et al. (1993). "Retinal pigment epithelial transplants and retinal function in RCS rats," Investigative Ophthalmology and Visual Science vol. 34, pp. 3068-3075.*

R.D. Lund et al. (2001). "Subretinal transplantation of genetically modified human cell lines attenuates loss of visual function in dystrophic rats," Proceedings of the National Academy of Sciences, U.S.A. vol. 98, pp. 9942-9947.*

R.D. Lund et al. (2003). "Retinal transplantation: progress and problems in clinical application," Journal of Leukocyt Biology vol. 74, pp. 151-160.*

A.A. Shvedova et al. (2003). "Exposure to carbon nanotube material: assessment of nanotube cytotoxicity using human keratinocyte cells," Journal of Toxicology and Environmental Health, Part A vol. 66, pp. 1909-1926.*

D.B. Warheit et al. (2004). "Comparative pulmonary toxicity assessment of single-wall carbon nanotubes in rats," Toxicological Sciences vol. 77, pp. 117-125.*

C.-W. Lam et al. (2004). "Pulmonary toxicity of single-wall carbon nanotubes in mice 7 and 90 days after intratracheal instillation," Toxicological Sciences vol. 77, pp. 126-134.*

Leng et al., "Carbon nanotube bucky paper as an artificial support membrane and Bruch's membrane patch in subretinal RPE and IPE transplantation", ARVO Annual Meeting Abstract Search and Program Planner, 2003, abstract 481, (2003).*

Woch, Gustaw, et al., Retinal Transplants Restore Visually Evoked Responses in Rats with Photoreceptor Degeneration, IOVS, Jun. 2001, 1669-1676, vol. 42, No. 7, Association for Research in Vision and Opthalmology.

\* cited by examiner

*Primary Examiner*—Sandra E. Saucier
(74) *Attorney, Agent, or Firm*—John F. Schipper; Robert M. Padilla

(57) ABSTRACT

A method for repairing a retinal system of an eye, using bucky paper on which a plurality of retina pigment epithelial cells and/or iris pigment epithelial cells and/or stem cells is deposited, either randomly or in a selected cell pattern. The cell-covered bucky paper is positioned in a sub-retinal space to transfer cells to this space and thereby restore the retina to its normal functioning, where retinal damage or degeneration, such as macular degeneration, has occurred.

7 Claims, 3 Drawing Sheets

BUCKY PAPER AS A SUPPORT MEMBRANE IN RETINAL CELL TRANSPLANTATION

FIELD OF THE INVENTION

This invention relates to use of an artificial substance as a support membrane for transplant of retinal and iris pigment epithelial cells and stem cells that can transform into these cells.

BACKGROUND OF THE INVENTION

Transplantation of retinal pigment epithelial (RPE) cells and iris pigment epithelial (IPE) cells, as a means to rescue or restore diseased photoreceptors in a sub-retinal space, is a leading experimental therapy for treating age-related macular degeneration (AMD), the most common form of blindness for persons over age 65 in Western nations. A sub-retinal space is a space adjacent to or underneath the retina, where the eye's photoreceptors are located.

The pathogenesis of AMD involves death of RPE cells at the posterior of the eye, underneath the retina in the sub-retinal space. The RPE membrane (Bruch's membrane) is also damaged in AMD because of new blood vessel growth and other factors related to normal aging. Death of the photoreceptor cells, and eventual blindness, follows death of the RPE cells.

One current theory suggests that replacement of dying RPE cells in the sub-retinal space may rescue or restore the function(s) of the photoreceptor cells. First attempts at RPE cell transplantation involved injecting a suspension of RPE cells into a patient's sub-retinal space. This approach was supplanted by transplant of intact sheets of RPE cells. Each of these techniques was plagued with problems arising from disorientation of the transplanted cells and from destruction of the Bruch's membrane in the AMD process.

One form of treatment of AMD is growth of RPE cells and/or IPE cells on a suitable support material and transplantation of cells and support material into the sub-retinal space of the eye. The RPE and IPE cells have been shown to survive after injection into the sub-retinal space as single cell suspensions, as patches of cells, and as sheets of confluent cells. However, the inability of these transplanted cells to spontaneously form an organized monolayer and perform phenotypic functions of native RPE cells may be a cause of ineffectiveness of this type of treatment. It has been suggested that transplanted RPE cells perform poorly in the pathological sub-retinal space because such cells attach poorly to a damaged Bruch's membrane of eyes affected by AMD. The Bruch's membrane can become damaged because of growth of new vessels. Transplantation of cell suspensions, or even of patches or confluent sheets of such cells, may be ineffective for AMD treatment.

One possible approach is to grow RPE and/or IPE on a suitable support material and to transplant both the cells and the support material into the sub-retinal space. Growth properties and related characteristics of pigment epithelial cells are greatly influenced by the surface properties of the substrate on which the cells are grown. Choroidal neovascularization, which is a characteristic of the wet/exudative form of AMD, may also be prevented by the support material by mechanical blockage. Additionally, use of support material will allow for transplantation of large sheets and monolayers of RPE and IPE. The surface of the support material may be modified to affect or control the growth properties of the transplanted RPE cells and/or IPE cells. The growth properties and characteristics of pigment epithelial cells are greatly influenced by the surface properties of the growth substrate. Several groups have studies different materials, such as anterior lens capsule and Descemet's membrane, for transplantation of RPE cells and IPE cells into the sub-retinal space. These attempts have been unsuccessful because of the handling properties of the support materials used by these experimenters. Although cells have been grown on lens capsule, it is difficult to implant lens capsule into the sub-retinal space, due to its tendency to curl on itself, especially in an aqueous environment. It is an even greater challenge to maintain lens capsule material flat when the material is implanted into the sub-retinal space. Additionally, use of a 10–15 µm thick lens capsule structure to replace a 2-µm thick layer of Bruch's membrane may pose some diffusion problems for the transplanted RPE and IPE cells and for the remaining retina. It is not yet known how porous lens capsule material and Descemet's membrane material are and whether these materials will allow for proper diffusion of nutrients, waste, oxygen and carbon dioxide.

What is needed is a support material that (1) is biocompatible, (2) will serve as a surface for growing selected cells or sheets of cells, (3) is moderately strong, (4) has a controllable range of porosity, and (5) will not spontaneously roll up or form creases.

SUMMARY OF THE INVENTION

These needs are met by a support material referred to as "bucky paper." Bucky paper is a mesh of carbon nanotubes (CNTs) whose thickness, density and/or porosity can be controlled in the manufacturing process. Bucky paper is made entirely of carbon and is biocompatible and capable of supporting growth of some biological substances. Because it is a mesh of CNTs, bucky paper is very porous and will allow nutrients, waste, oxygen and carbon dioxide to diffuse relatively easily through the CNT mesh, irrespective of thickness. Bucky paper can be made rigid, but can still be able to conform to the shape of the inner retina with appropriate fabrication. Bucky paper will allow for great precision during surgical handling and will remain relatively flat against the choroid when the combination of bucky paper and RPE cells or IPE cells or stem cells are transplanted into the sub-retinal space. When properly prepared, bucky paper will serve simultaneously as a substrate for cell growth and as a barrier for selectively preventing growth of unwanted biological tissues, such as blood vessels.

DESCRIPTION OF BEST MODES OF THE INVENTION

The invention provides rescue or restoration of the diseased photoreceptor cell layer of the retina, using transplantation of RPE cells, IPE cells or stem cells on bucky paper to the sub-retinal space of the eye. The bucky paper serves as a physical support for the transplanted cells and as a basement membrane patch. Preparation of the bucky paper itself is discussed following discussion of use of the bucky paper for the cell transplantation.

Cell Culture. Human RPE cells for transplantation were maintained in D-MEM/F-12 solution, supplemented with 10 percent fetal bovine serum at T=37° C. with 6.5 percent $CO_2$. The cells were removed from 100 mm tissue culture dishes with 0.05 percent trypsin-EDTA and were cultured weekly at a 1:10 ratio. A concentration of $10^6$ cells/mL was cultured onto sterilized bucky paper. Stem cells that can transform or differentiate into RPE cells can also be transplanted here.

Animal IPE cells were harvested and isolated from New Zealand White rabbits, using an enzyme-assisted microdissection procedure described by Hu and McCormick, in Arch. Ophthalmol., vol. 115 (1997) pp. 89–94. The primary culture was maintained in an F-12 Nutrient Mixture (HAM) with L-glutamine supplemented with 20 percent fetal bovine serum and 50 μg/mL gentamicin. The maintenance media were exchanged every three days. Primary cultures of IPE cells were cultured onto sterile bucky paper at $10^6$ cells/mL. All cell reagents were obtained from Life Technologies, Inc. in Rockville, Md.

Figure 1:
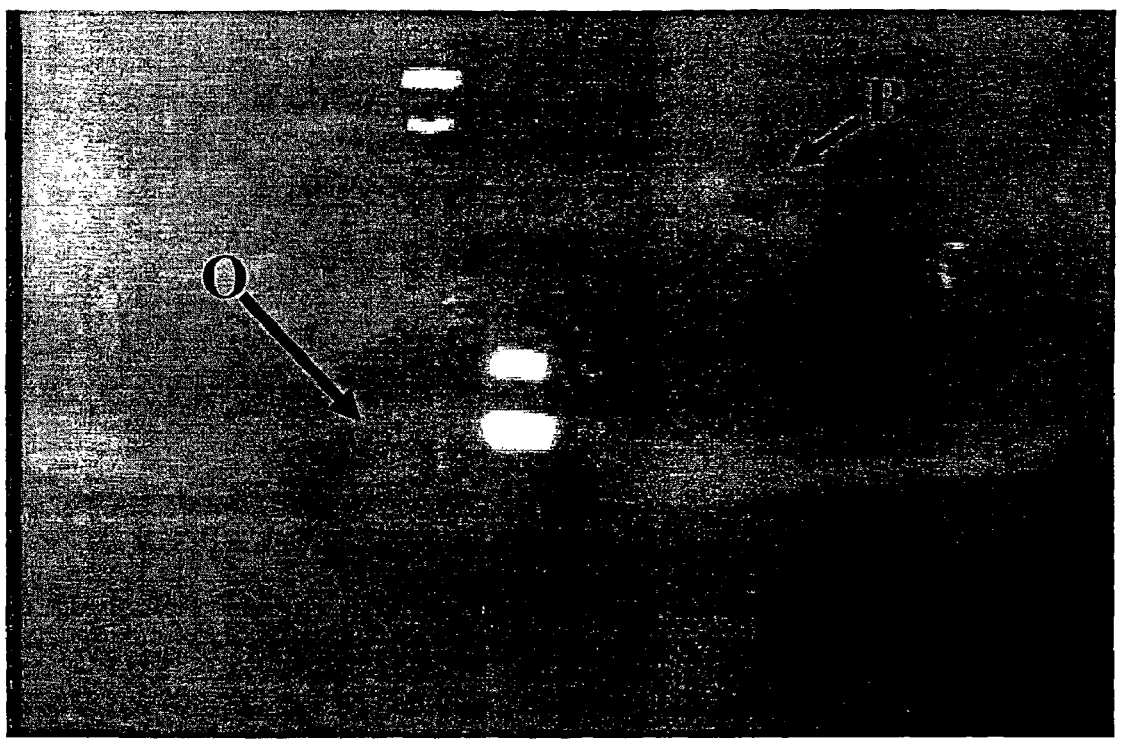
FIG. 1 is a photographic image of a reattached retina of a White Rabbit's eye after the experimental procedure described herein.

Surgical Technique. Bucky paper was implanted into the sub-retinal space of New Zealand White rabbits, each weighing 2.5–3.5 kg. The rabbits were anesthetized with ketamine (40 mg/kg) and Xylazine (5 mg/kg), administered through intramuscular injection. One dose of Tropicamide 0.5 percent eye drops and Phenylephrine 2.5 percent eye drops were instilled into the conjunctival sac of the left eye. Standard three-port pars plana vitrectomy was performed, and a retinal bleb was inflated in the macular area by injection of approximately 0.5 mL of balanced salt solution (BSS) through a 42-gauge needle. A retinotomy 1 mm in diameter was created, using a delaminating knife, and the bucky paper was inserted into the sub-retinal space through the aperture. The retina was then reattached through air-fluid exchange. FIG. 1 is a photograph of a reattached retina. The care of the animals conformed to the ARVO Statement for the *Use of Animals in Ophthalmic and Vision Research*, and the Administrative Panel on Laboratory Animal Care at Stanford University approved the protocol (No. 6597) employed.

Figure 2:
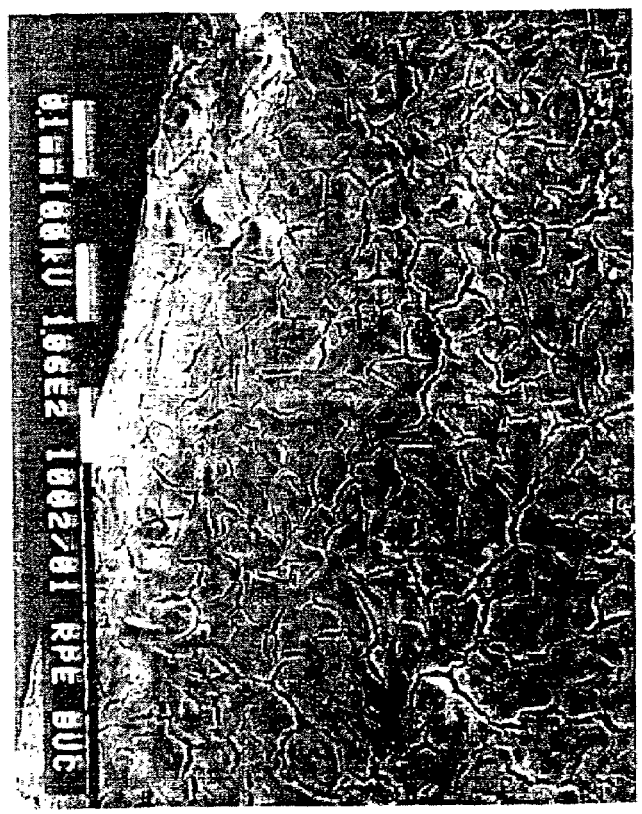
FIG. 2 is an SEM image of human RPE cells cultured onto a bucky paper surface.

Microscopy. FIG. 2 is an SEM image of human RPE cells cultured onto a bucky paper surface, using the described technique. SEM images were obtained by fixing the cells in 5 percent glutaraldehyde/2 percent paraformaldehyde in 0.1 M sodium cacodylate buffer (pH=7.4), for 3 hours. The cells were washed in sodium cacodylate (0.1 M, pH=7.4) and were post-fixed in 1 percent osmium tetroxide for 3 hours at T=4° C. and dehydrated, dried at the critical point and sputter coated with gold. All electron microscopy materials were obtained from EM Sciences, Fort Washington, Pa.

Histology. Rabbit eyes were enucleated one and two weeks after inoculation. The eyes were fixed in 1.25 percent glutaraldehyde/1 percent paraformaldehyde in cacodylate buffer (pH=7.4). After fixation, the eyes were cut open, fixed, post-fixed in osmium tetroxide, dehydrated with a graded series of EtOH, and embedded in epoxy resin. Sections of 1 μm thickness were stained with toluidine blue for improved contrast.

Bucky Paper Preparation. The bucky paper used in the experiments disclosed here was fabricated at the N.A.S.A. Ames Research Center Nanofabrication Facility in Moffett Field, Calif. Carbon nanotube (CNT) bucky paper is prepared from crude preparations of single wall carbon nanotubes (SWCNTs) synthesized by a laser ablation technique, available from commercial sources. Other preparations of SWCNTs or multi-wall carbon nanotubes (MWCNTs), such as those synthesized by the well known HiPCO technique (a high pressure process using carbon monoxide) are also acceptable. The crude preparation is first purified by refluxing in nitric acid for 160 hours and the resulting product is centrifuged. A pellet (resulting from centrifugation) is suspended in potassium hydroxide solution (pH=10), then washed twice by centrifugation and re-suspension. The purified CNTs are washed twice in distilled water, using centrifugation and re-suspension. The purified CNTs are re-suspended in distilled water, then mechanically formed into bucky paper by removal of water by vacuum filtration over a cellulose filter or similar filter. Portions of the CNTs incorporated in the bucky paper produced here may be "bundled", or partially or fully aligned, due to liquid flow through the mesh of CNTs, which may provide a higher than normal density of CNTs in an array.

Figure 3:
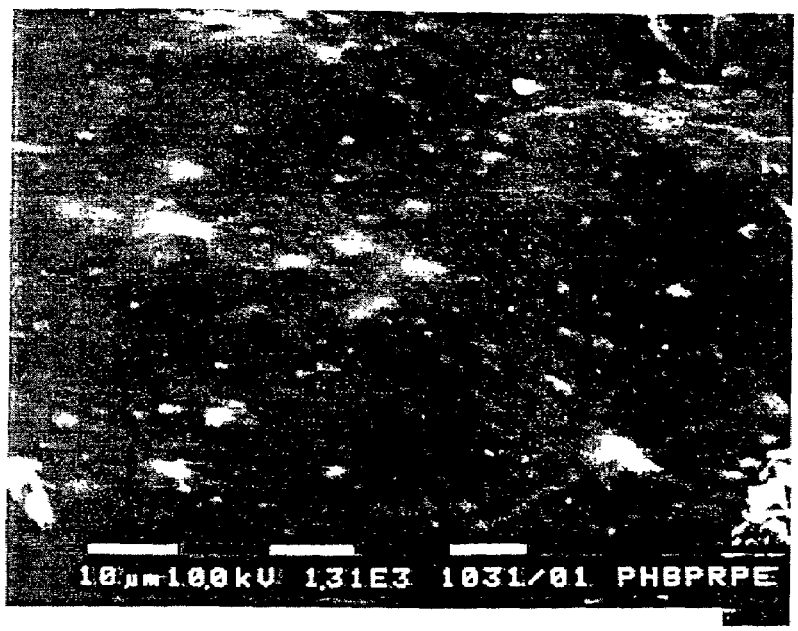
FIG. 3 is a scanning electron microphotograph (SEM) image of a bucky paper scrap after fabrication.

This bucky paper used in the experiments discussed here had a thickness in the range of 50–100 μm and an area density in the range of 700–1500 μgm/$cm^2$. In one approach, bucky paper is prepared by immobilizing 1 cm×0.5 cm bucky paper on sterilized wax strips, using copper pins. The bucky paper, after mounting, was itself sterilized by immersion in 70 percent EtOH for 300 sec and subsequent exposure to ultraviolet light for about 3 hours. FIG. 3 is a scanning electron microphotograph (SEM) image of a bucky paper scrap after fabrication. Separate procedures are optionally provided for generating and controlling patterns or densities of growth of an array of single wall nanotubes or multi-wall nanotubes, with a carbon nanotube (CNT) length that depends upon the structure involved. A CNT can be grown with a length between about 25 μm and 200 μm, or longer if desired. However, control of the length of the CNTs may not be important for bucky paper applications. The desired support material (bucky paper) will preferably form a mesh or mat. The mesh thickness h(mesh) and mesh density partly determine the bucky paper porosity. A mesh density range of $4 \times 10^6$–$6 \times 10^1$/$cm^2$, corresponding to a range d=40 nm–5 μm for average nearest neighbor center-to-center separation distance is produced where a substrate is not used for CNT growth. Use of a higher bucky paper average thickness h may require use of a higher separation distance d, to preserve similar bucky paper behavior.

Cell Patterning on Bucky Paper. Enhancement of RPE cell and/or IPE cell and/or stem cell attachment to bucky paper can be accomplished by chemical modification of the bucky paper surface (addition of hydrogen, nitrogen and/or oxygen molecules) or by adsorption or covalent attachment of specific growth factors and/or cytokines and/or antibodies and/or extracellular matrix proteins (such as CNTF, polylysine, collagen, fibronectin, laminin, brain-derived neurotrophic factor, ciliary neurotrophic factor, nerve growth factor, forskolin, inhibitors of myelin-associated glycoprotein and inhibitors of NOGO). If necessary, the adsorption of specific growth factors and/or cytokines and/or antibodies and/or extracellular matrix proteins to the bucky paper can be stabilized by partial or complete cross-linking of these specific growth factors and/or cytokines and/or antibodies and/or extracellular matrix proteins to one another, rather than by direct binding to the CNT elements of the bucky paper.

In addition these specific growth factors and/or cytokines and/or antibodies and/or extracellular matrix proteins can be applied to the bucky paper surface in a specific pattern, such as a grid or geometric arrangement, in situations where a pattern of RPE cell and/or IPE cell and/or stem cell attachment to the bucky paper may be advantageous, as compared to homogeneous, unpatterned attachment of cells. Patterning of specific growth factors and/or cytokines and/or antibodies and/or extracellular matrix proteins may also facilitate attachment of combinations of RPE cells, IPE cells and/or stem cells to the bucky paper surface, as compared to single populations of cells; transplantation of combinations of cell types may achieve superior results in restoring retinal function a compared to transplantation of only one cell type.

Figure 4:
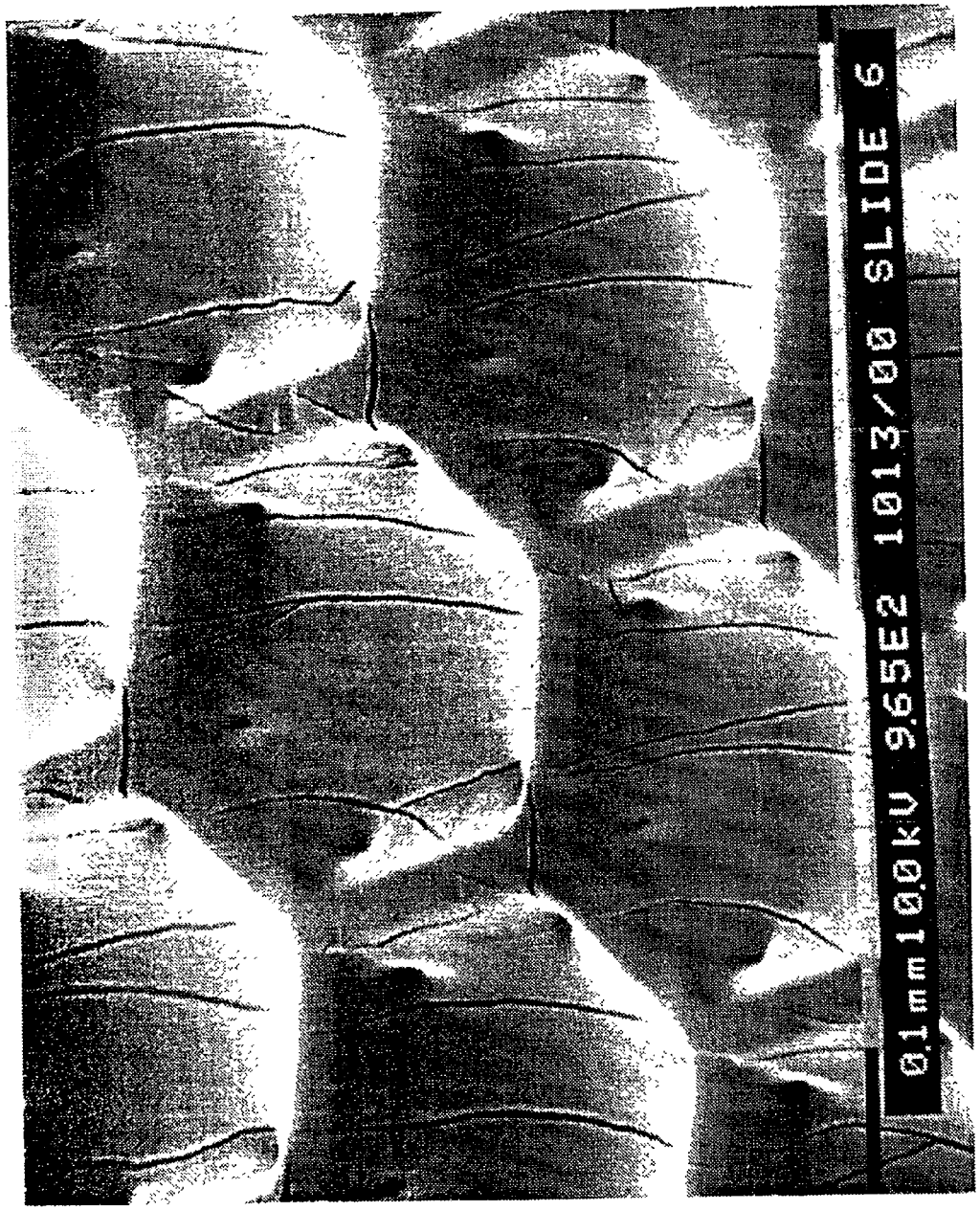
FIG. 4 is a photomicrograph of a typical CNT pattern used on bucky paper.

One attractive pattern is a grid-like hexagonal pattern, illustrated in a photomicrograph shown in FIG. 4, where a side of the hexagonal array has a length in the range of 50–100 μm. In this approach, one challenge is to deposit the RPE and/or IPE cells and/or stem cells with precision, allowing little or no spillover of the cells into the interstitial region that are preferably barren. More generally, the pattern for the RPE cells, the IPE cells and/or the stem cells transferred to or deposited on the bucky paper may be a triangle, a quadrilateral (including squares, rectangles and trapezoids), a pentagon, a hexagon, an n-sided polygon ($n \geq 7$), a circle, an oval, or a general convex, two-dimensional figure.

The vacuum filtration device includes a solid support surface, with apertures therein for vacuum filtering, and a filter paper positioned to prevent loss of the CNTs through the apertures. The vacuum filtration process used to fabricate the bucky paper often leaves a pattern of dimples, representing the filter aperture pattern, on the bucky paper. This pattern can be used to provide an array of sites for the RPE, IPE and/or stem cells to be deposited on the paper, by providing a filter aperture pattern that matches the desired pattern of cell sites. The filter aperture pattern need not be uniform and may have regions where no apertures are present and other regions where a relatively high density of apertures is present. The solid support material of the filtration device is usually a rigid material so that a filter with the desired aperture pattern can be fabricated and will hold the aperture pattern for repeated use, if desired. The filter paper, placed over the solid support material and apertures of the filtration device, is chosen to be flexible, in order to conform to and replicate the aperture pattern on the bucky paper as the paper is formed.

What is claimed is:

1. A method for preparing a retinal system of an eye for repair, the method comprising:
   providing a support material, comprising bucky paper having a selected thickness and a selected porosity, as a patch having a selected size;
   transferring at least one of (i) a retinal pigment epithelial cell, referred to as an RPE cell, (ii) an iris pigment epithelial cell, referred to as an IPE cell and (iii) a stem cell, to the support material, to provide a cell-covered support material; and
   attaching the cell-covered support material to a selected region in a sub-retinal space of an eye that is to be repaired.

2. The method of claim 1, wherein said step of providing said bucky paper comprises:
   using a high pressure carbon monoxide process to prepare a plurality of single-wall and multi-wall carbon nanotubes (referred to as "CNTs");
   immersing the plurality of CNTs in a selected acid for a selected time interval, and allowing the CNTs to become purified;
   centrifuging the CNTs at least once to form at least one pellet containing primarily CNTs;
   suspending the CNT pellet at least once in a selected base for a selected time interval;
   immersing the CNT pellet in distilled water;
   removing substantially all liquid from the CNT pellet by:
      providing a solid support filter having an array of filter apertures therein in a selected pattern;
      providing a filter paper, having a selected porosity, contiguous to the filter apertures;
      positioning the CNT pellet adjacent to the filter paper so that the filter paper lies between the CNT pellet and the filter; and
      applying a selected vacuum to the filter and filter apertures so that liquid associated with the CNT pellet is removed from the CNT pellets through the filter paper and through at least one filter aperture;
   mechanically forming the CNT pellet into at least one scrap of said bucky paper; and
   allowing at least one dimple to form in a surface of said bucky paper adjacent to a location of one of said apertures in said solid support filter.

3. The method of claim 1, wherein said step of providing said cell-covered support material comprises:
   transferring a plurality of at least one of a collection of RPE cells and a collection of IPE cells and a collection of stem cells in a selected pattern to said support material.

4. The method of claim 3, wherein said step of attaching said cell-covered support material to said selected region in said sub-retinal space comprises:
   pressing said cell-covered support material against said selected region in said sub-retinal space so that said cell-covered support material becomes mechanically attached to said selected region.

5. The method of claim 3, wherein said step of attaching said cell-covered support material to said selected region in said sub-retinal space comprises:
   pressing said cell-covered support material against said selected region in said sub-retinal space so that at least one of said RPE cells, said IPE cells and said stem cells on said cell-covered support material becomes mechanically attached to said selected region.

6. The method of claim 3, further comprising selecting said pattern from the group of patterns consisting of triangles, quadrilaterals, pentagons, hexagons, n-sided polygons, with n at least equal to 7, circles and ovals.

7. The method of claim 1, wherein said step of providing said cell-covered support material comprises:
   providing said bucky paper in a selected pattern on said support material, the selected pattern comprising at least two connected regions of bucky paper separated by at least one interstitial region that is substantially free of bucky paper, where said selected thickness of said bucky paper lies in a range 25–200 μm; and
   transferring a liquid solution containing at least one of said RPE cells, said IPE cells and said stem cells to the at least two connected regions of bucky paper so that the at least one interstitial region has substantially no liquid solution thereon,
   whereby the at least one of said RPE cells, said IPE cells and said stem cells is attached to the at least two connected regions of bucky paper and is not attached to the at least one interstitial region.

* * * * *